US009034274B2

(12) United States Patent
Shinoda et al.

(10) Patent No.: US 9,034,274 B2
(45) Date of Patent: May 19, 2015

(54) VEHICULAR AIR CLEANER

(75) Inventors: Yoshihisa Shinoda, Susono (JP); Kazuhiro Sugimoto, Susono (JP); Hiroaki Katsumata, Susono (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 0 days.

(21) Appl. No.: 14/002,150

(22) PCT Filed: Mar. 23, 2011

(86) PCT No.: PCT/JP2011/056929
§ 371 (c)(1),
(2), (4) Date: Aug. 29, 2013

(87) PCT Pub. No.: WO2012/127645
PCT Pub. Date: Sep. 27, 2012

(65) Prior Publication Data
US 2014/0186222 A1    Jul. 3, 2014

(51) Int. Cl.
| | |
|---|---|
| *B01J 20/34* | (2006.01) |
| *B01J 31/00* | (2006.01) |
| *C09K 3/22* | (2006.01) |
| *A61L 9/00* | (2006.01) |
| *B01D 53/86* | (2006.01) |

(52) U.S. Cl.
CPC .............. *A61L 9/00* (2013.01); *B01D 53/8675* (2013.01); *B01D 2255/1021* (2013.01); *B01D 2255/1023* (2013.01); *B01D 2255/1025* (2013.01); *B01D 2255/1026* (2013.01); *B01D 2255/104* (2013.01); *B01D 2255/106* (2013.01); *B01D 2255/2073* (2013.01); *B01D 2255/20738* (2013.01); *B01D 2255/20746* (2013.01); *B01D 2255/20753* (2013.01);
(Continued)

(58) Field of Classification Search
CPC ............... A61L 9/00; A61L 9/014; B01J 2/00
USPC ............. 422/28, 30, 122, 177, 211, 239, 312, 422/900; 95/138; 502/34, 60, 100, 173, 502/400; 252/88.2; 205/701, 742, 756; 96/62, 67
See application file for complete search history.

(56) References Cited

U.S. PATENT DOCUMENTS

| | | | |
|---|---|---|---|
| 4,207,291 A | | 6/1980 | Byrd et al. |
| 7,582,270 B2 * | | 9/2009 | Zuberi .......................... 423/210 |

(Continued)

FOREIGN PATENT DOCUMENTS

| | | |
|---|---|---|
| CN | 101138703 | 3/2008 |
| JP | 2002-514966 | 5/2002 |

(Continued)

*Primary Examiner* — Monzer R Chorbaji
(74) *Attorney, Agent, or Firm* — Finnegan, Henderson, Farabow, Garrett & Dunner, LLP

(57) ABSTRACT

The present invention relates to a vehicular air cleaner. A DOR (Direct Ozone Reduction) system for suppressing deterioration of a purifying function of an ozone purifying material is provided. Active oxygen is produced by an ozone purifying function of activated carbon. The probability that the active oxygen contacts with a fin of a radiator on a rear surface side is higher than that on a front surface side of the radiator. Accordingly, the activated carbon on the rear surface side of the radiator is easily oxidized as compared with the activated carbon on the front surface side. Therefore, in the fin, a coating amount of the activated carbon on the front surface side of the radiator is adjusted to be larger than a coating amount of the activated carbon on the rear surface side. Thus, the probability that the active oxygen contacts with the activated carbon can be reduced.

7 Claims, 10 Drawing Sheets

(52) U.S. Cl.
CPC .. *B01D 2255/20761* (2013.01); *B01D 2255/50* (2013.01); *B01D 2257/106* (2013.01); *B01D 2258/06* (2013.01); *B01D 2259/4566* (2013.01); *Y10S 422/90* (2013.01)

(56) References Cited

U.S. PATENT DOCUMENTS

2005/0191223 A1 9/2005 Collins et al.
2006/0182669 A1 8/2006 Matumura et al.
2008/0010972 A1 1/2008 Ikeda

FOREIGN PATENT DOCUMENTS

| | | |
|---|---|---|
| JP | 2006-231324 | 9/2006 |
| WO | WO 96/22146 A1 | 7/1996 |
| WO | WO 96/22150 | 7/1996 |
| WO | WO 98/02235 | 1/1998 |

\* cited by examiner (A)

(B)

VEHICULAR AIR CLEANER

CROSS-REFERENCE TO RELATED APPLICATIONS

This application is a national phase application of International Application No. PCT/JP2011/056929, filed Mar. 23, 2011, the content of which is incorporated herein by reference.

TECHNICAL FIELD

The present invention relates to a vehicular air cleaner and, more particularly, to a vehicular air cleaner capable of purifying ozone in air.

BACKGROUND ART

Ozone, which causes photochemical smog, is produced by a photochemical reaction of HC and NOx contained in exhaust gases from automobiles and factories. Therefore, reducing the amount of HC and NOx emissions from automobiles is an efficient way to suppress the production of ozone and the occurrence of photochemical smog. Also, purifying ozone in the air directly can be one of the ways to prevent the occurrence of photochemical smog. By purifying ozone as a product as well as reducing the amount of emissions of HC and NOx as reactants, the occurrence of photochemical smog can be prevented more effectively. Thus, an automobile including a vehicular air cleaner capable of directly purifying ozone in the air has been put into practical use in some places including California in the United States of America. Such a vehicular air cleaner is called a DOR (Direct Ozone Reduction) system.

For example, Patent Literature 1 discloses a DOR system in which a vehicle component part carries metal oxide such as manganese dioxide. The vehicle component part is arranged at the position where the part is exposed to air, and the manganese dioxide has a function for converting ozone contained in the air into other substances such as oxygen and purifying the ozone. Thus, according to the DOR system disclosed in Patent Literature 1, ozone in air can be directly purified while a vehicle is moving.

CITATION LIST

Patent Literature

Patent Literature 1: National Publication of International Patent Application No. 2002-514966
Patent Literature 2: Japanese Patent Laid-Open No. 2006-231324

SUMMARY OF INVENTION

It has been known that not only metal oxide such as manganese dioxide but also activated carbon and elemental metal have a function for purifying ozone. Since the activated carbon and the elemental metal have the function for purifying ozone as well as the metal oxide and are available at moderate price, they have been expected to be used as an alternative to the metal oxide. Especially, the activated carbon can purify ozone at ambient temperature (25° C.) and thus has an advantage over the metal oxide which purifies ozone at a higher temperature than the ambient temperature. However, there is a problem where the activated carbon or elemental metal is used as an ozone purifying material, its ozone purifying function is easily deteriorated.

The reason why the ozone purifying function of the activated carbon or elemental metal is easily deteriorated can be made clear by considering how the function works. When the activated carbon or elemental metal dissolves ozone, active oxygen may be produced in addition to oxygen. Since the active oxygen has stronger oxidizing power than the ozone, it easily reacts with the activated carbon or elemental metal to oxidize it. Accordingly, when the activated carbon or elemental metal is simply applied to the DOR system, a vehicle component part carrying it needs to be exchanged frequently. Thus, it is not practical and needs further improvement.

The present invention has been made in view of the above-described circumstances. It is an object to provide a DOR system which suppresses deterioration of a purifying function of an ozone purifying material.

Means for Solving the Problem

To achieve the above mentioned purpose, a first aspect of the present invention is a vehicular air cleaner, comprising:

a vehicle component part including an air inlet into which air is delivered during travel of a vehicle, an air outlet through which the air delivered from the air inlet is discharged, and an inner flow path connecting the air inlet and the air outlet; and an ozone purifying material carried on a wall surface of the inner flow path for purifying ozone by converting the ozone into other substances, wherein an amount of the carried ozone purifying material is adjusted such that the amount of the carried ozone purifying material on the air inlet side is larger than that on the air outlet side.

A second aspect of the present invention is the vehicular air cleaner according to the first aspect, further comprising an ozone purifying catalyst which is carried on the wall surface of the inner flow path and produced by a purifying function of the ozone purifying material, the ozone purifying catalyst having resistance to an oxidant which oxidizes the ozone purifying material while purifying the ozone by converting the ozone into other substances.

A third aspect of the present invention is the vehicular air cleaner according to the second aspect, wherein an amount of the carried ozone purifying catalyst is adjusted such that the amount of the carried ozone purifying catalyst on the air outlet side is larger than that on the air inlet side.

A forth aspect of the present invention is the vehicular air cleaner according to the second or the third aspect, wherein the ozone purifying catalyst includes at least one of a metal complex and a metallo-organic complex composed of manganese, iron, cobalt, nickel, copper, ruthenium, rhodium, or palladium as a center metal, palladium, silver, platinum, gold, and zeolite.

A fifth aspect of the present invention is the vehicular air cleaner according to any one of the first to the forth aspects, wherein a specific surface area of the ozone purifying material is adjusted such that the specific surface area on the air outlet side is larger than that on the air inlet side.

A sixth aspect of the present invention is the vehicular air cleaner according to any one of the first to the fifth aspects, wherein the vehicle component part is a radiator.

A seventh aspect of the present invention is vehicular air cleaner according to the sixth aspects, wherein the radiator includes a fin formed with louvers imparting turbulence to the air delivered from the air inlet.

A eighth aspect of the present invention is vehicular air cleaner according to the sixth or the seventh aspect, wherein the radiator includes a cooling water path for delivering cooling water therein, and the amount of the carried ozone purifying material is adjusted such that the amount of the carried ozone purifying material on an outlet side of the cooling water path is larger than that on an inlet side of the cooling water path.

A ninth aspect of the present invention is vehicular air cleaner according to any one of the first to the eighth aspects, wherein the ozone purifying material includes at least one of activated carbon, manganese, iron, cobalt, nickel, copper, ruthenium, and rhodium.

Advantageous Effects of Invention

Since the active oxygen is produced due to the purifying function of the ozone purifying material, the amount of the active oxygen on the air outlet side is larger than that on the air inlet side. Accordingly, the probability that the ozone purifying material is oxidized by the active oxygen on the air outlet side is higher than that on the air inlet side. According to the first aspect of the present invention, the amount of the carried ozone purifying material is adjusted such that the amount of the carried ozone purifying material on the air inlet side is larger than that on the air outlet side. Therefore, the probability that the active oxygen contacts with the ozone purifying material on the air outlet side can be reduced. Thus, the deterioration of the purifying function of the ozone purifying material can be suppressed and therefore the longevity of the vehicle component part can be lengthened.

When the amount of the carried ozone purifying material on the air outlet side is reduced, the ozone purifying capability is reduced. According to the second aspect of the present invention, the ozone purifying catalyst exhibits resistance to the oxidant such as active oxygen and has a function for converting the ozone into other substances and purifying the ozone. Thus, the reduction of the ozone purifying capability can be compensated by the ozone purifying catalyst.

According to the third aspect of the present invention, the amount of the carried ozone purifying catalyst is adjusted such that the amount of the carried ozone purifying catalyst on the air outlet side is larger than that on the air inlet side. Thus, the reduction of the ozone purifying capability by reducing the amount of the carried ozone purifying material can be favorably compensated.

According to the fourth aspect of the present invention, the wall surface of the inner flow path preferably support as the ozone purifying catalyst including at least one of metal complex and metallo-organic complex composed of manganese, iron, cobalt, nickel, copper, ruthenium, rhodium, or palladium as a center metal, palladium, silver, platinum, gold, and zeolite.

The ozone purifying capability is higher as the specific surface area of the ozone purifying material is larger. According to the fifth aspect of the present invention, the specific surface area of the ozone purifying material is adjusted such that the specific surface area on the air outlet side is larger than that on the air inlet side. Thus, the reduction of the ozone purifying capability by reducing the amount of the carried ozone purifying material can be compensated.

According to the sixth aspect of the present invention, the energy required for ozone purifying reaction can be obtained by heat exchange with the cooling water. Thus, the ozone purification can be promoted.

When the air flowing through the inner flow path becomes turbulent, the flow rate becomes slow. Thus, the air containing the oxidant such as active oxygen is associated with a high probability of contacting with the ozone purifying material. Especially, in the radiator including the fin formed with the louvers, the turbulent flow of the air is remarkably produced. According to the seventh aspect of the present invention, the deterioration of the purifying function can be suppressed even when the ozone purifying material is applied to such a radiator.

In the radiator formed with the cooling water path, the cooling water at high temperature is delivered into the inlet of the cooling water path. Accordingly, the reactivity of the ozonolysis reaction on the inlet side of the cooling water path is higher than that on the outlet side. Thus, the amount of produced active oxygen on the inlet side of the cooling water path is larger than that in the ozone purifying material close to the outlet side. In other words, the probability of contacting with the active oxygen on the downstream of the ozone purifying material close to the inlet of the cooling water path is high. According to the eighth aspect of the present invention, the amount of the carried ozone purifying material is adjusted such that the amount of the carried ozone purifying material on an outlet side of the cooling water path is larger than that on an inlet side of the cooling water path. Thus, the deterioration of the purifying function of the ozone purifying material on the downstream of the cooling water path can be favorably suppressed.

According to the ninth aspect of the present invention, the wall surface of the inner flow path preferably support as the ozone purifying material including at least one of activated carbon, manganese, iron, cobalt, nickel, copper, ruthenium, and rhodium.

DESCRIPTION OF EMBODIMENTS

First Embodiment

Figure 1:
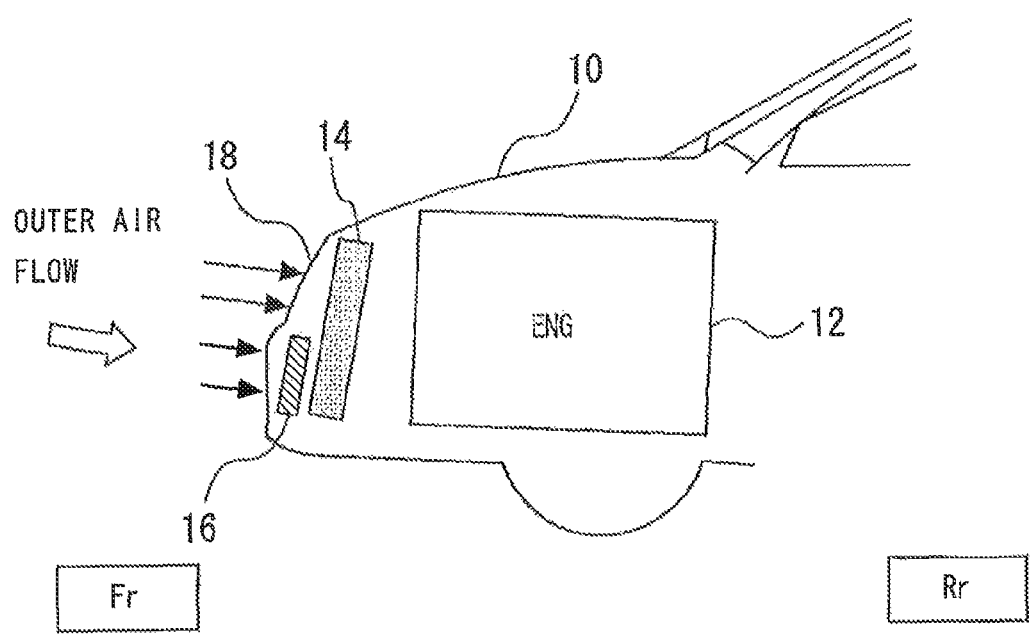
FIG. 1 is a schematic view showing a structure of a vehicle 10 on which an air cleaner according to each embodiment of the present invention is applied.

A first embodiment of the present invention will be explained below with reference to FIGS. 1 to 8. FIG. 1 is a schematic view showing a structure of a vehicle on which an air cleaner is mounted according to the first embodiment. The vehicle 10 includes an internal combustion engine 12 serving as a power unit. The exhaust gas discharged from the internal combustion engine 12 contains HC and NOx. Ozone is produced by photochemical reaction between HC and NOx as reactants. Therefore, the air cleaner is mounted on the vehicle 10 including the internal combustion engine 12, the ozone is purified while the vehicle 10 is moving, and thus, the damage to the environment caused due to the vehicle 10 can be reduced.

A radiator 14 for cooling coolant water circulating through the internal combustion engine 12 is arranged on the front side of the internal combustion engine 12. A capacitor 16 of an air conditioner is mounted on the front side of the radiator 14. As shown by arrows in FIG. 1, outer air is taken in through a bumper grill 18 arranged on a front surface of the vehicle 10 during travel of the vehicle 10 and the taken air is delivered through the capacitor 16 and the radiator 14 in this order to be discharged to the rear side.

Figure 2:
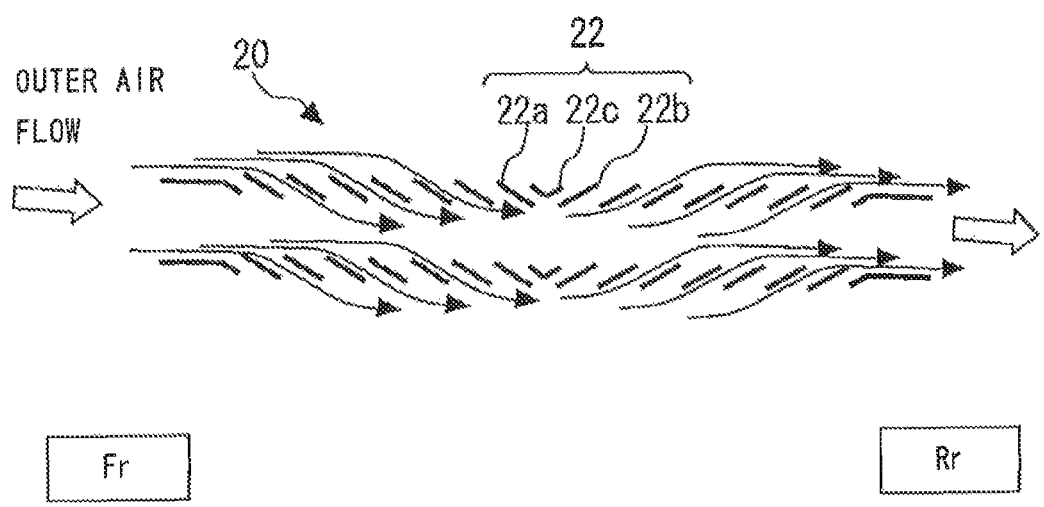
FIG. 2 is a cross-sectional view of a radiator 14.

A louvered-fin is provided at the core of the radiator 14. FIG. 2 is a cross-sectional view of the radiator 14. As shown in FIG. 2, a plurality of louvers 22 is formed on the fin 20 of the radiator 14. The louvers 22 include slant pieces 22a and 22b slanted relative to the direction where the air is delivered and a bent piece 22c. The arrangement of louvers 22 makes it possible to increase the pressure loss of the air delivered through the radiator 14, and thus to reduce its flow rate and to generate its secondary flow. Thus, the heat-transfer performance of the radiator 14 can be improved.

The air cleaner according to the first embodiment is provided by coating the fin 20 shown in FIG. 2 with activated carbon. In the first embodiment, the coating amount of the activated carbon on the front surface side of the radiator 14 is adjusted to be larger than the coating amount of the activated carbon on the rear surface side. The reason why the coating amount is adjusted in such a manner will be explained below with reference to FIGS. 3 to 5.

Figure 3:
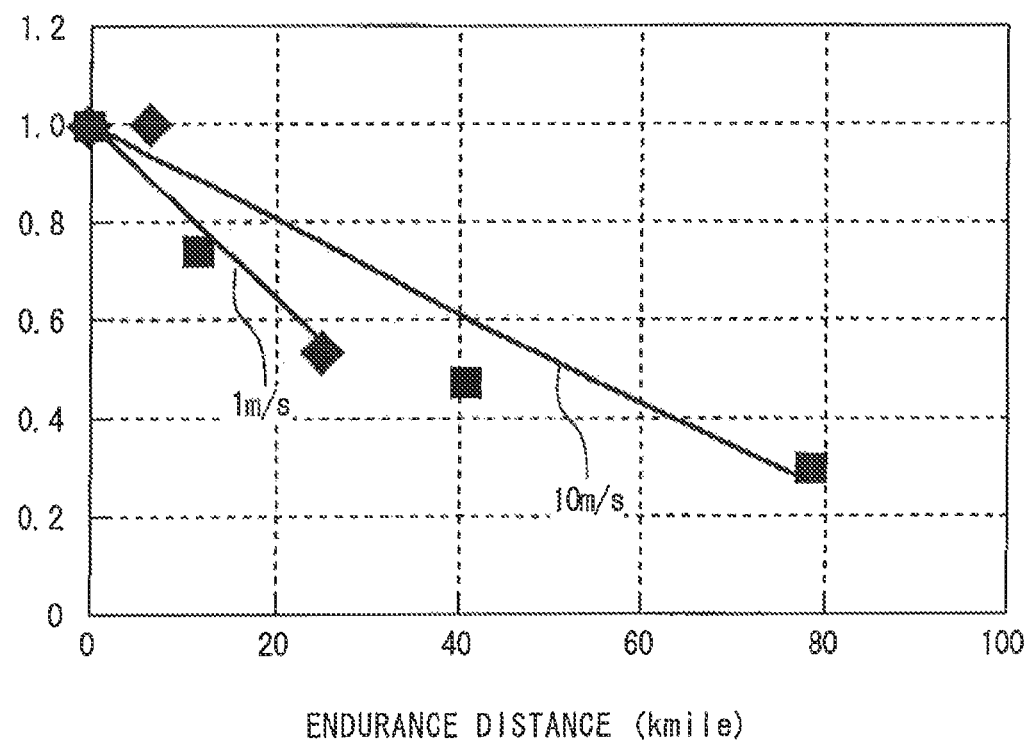
FIG. 3 shows data of results of an ozone purification endurance test.

FIG. 3 shows data of results of an ozone purification endurance test. In FIG. 3, the horizontal axis represents an endurance distance (kilomile) and the vertical axis represents a relative value based on an ozone purification rate at an initial state (when the endurance distance is 0 kilomile). The data shown in FIG. 3 is obtained by preparing two activated carbons of equivalent sizes and specific surface areas, and then measuring the rear side ozone concentration of these activated carbons when a gas containing ozone having a predetermined concentration passes through these activated carbons from the front side toward the rear side at different velocities (wind velocities of 1 m/s and 10 m/s).

As shown in FIG. 3, the ozone purification rate of the activated carbon is reduced as the endurance distance becomes longer. Also, as shown in FIG. 3, the degree of reduction of the ozone purification rate of the activated carbon is changed depending on the wind velocity of the passing gas containing ozone. More specifically, in the case where the gas containing ozone passes at the wind velocity of 1 m/s, the ozone purification rate goes down by half from the ozone purification rate at the initial state when the endurance distance is approximately 30 kilomiles. In the case where the gas containing ozone passes at the wind velocity of 10 m/s, the ozone purification rate remains at about 70% or more of the ozone purification rate at the initial state when the endurance distance is approximately 30 kilomiles, and then goes down by half when the endurance distance is approximately 60 kilomiles. In other words, the degree of reduction of the ozone purification rate is smaller when the gas passes at high speed (wind velocity of 10 m/s) as compared to when the gas passes at low speed (wind velocity of 1 m/s).

Figure 4:
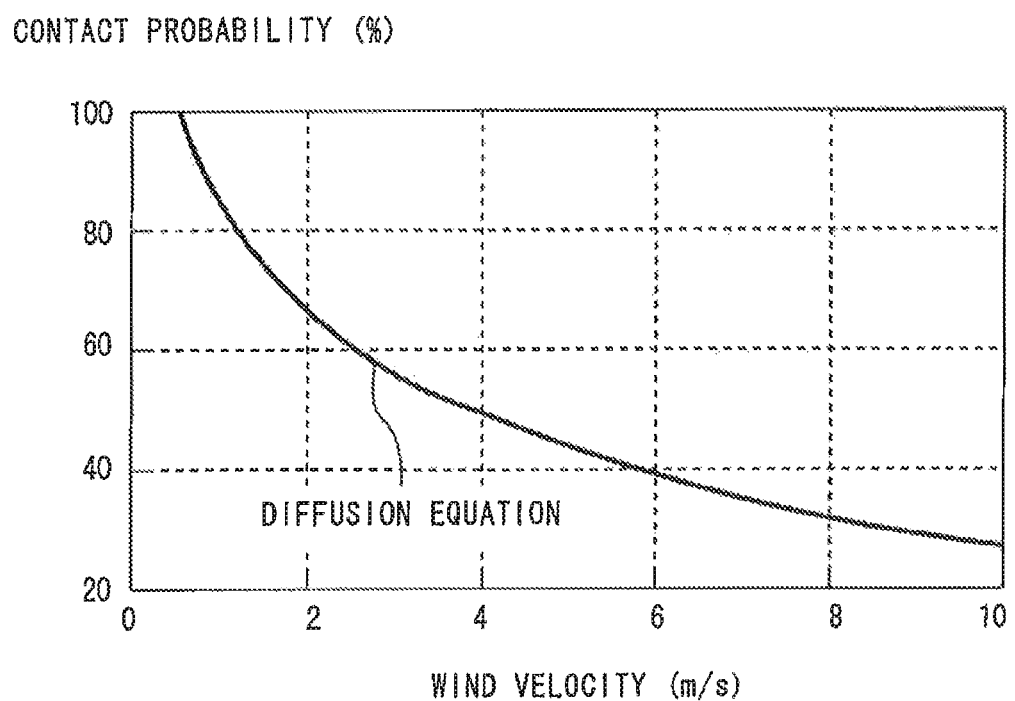
FIG. 4 is a graph showing a relationship between the wind velocity of a gas passing through the radiator and the probability that the gas contacts with the radiator.

FIG. 4 is a graph showing a relationship between the wind velocity of a gas passing through a radiator and the probability that the gas contacts with the radiator (hereinafter referred to as "gas contact probability"). This graph is provided by applying the Gormley-Kennedy diffusion equation to a model of an aluminum honeycomb radiator. As shown in FIG. 4, the gas contact probability is approximately 100% when the wind velocity is approximately 1 m/s. Also, the gas contact probability is approximately 10% when the wind velocity is approximately 10 m/s. In other words, the gas contact probability is high when the wind velocity is slow, and is gradually lowered as the wind velocity is faster.

From the graphs shown in FIGS. 3 and 4, it is found that the ozone purification rate and the gas contact probability correlate with each other. It is found from FIG. 4 that the gas contact probability is higher as the wind velocity is slower and the gas contact probability is lower as the wind velocity is faster. Also, it is found from FIG. 3 that the degree of reduction of the ozone purification rate is larger as the wind velocity is slower and the degree of reduction of the ozone purification rate is smaller as the wind velocity is faster. Thus, from the graphs in FIGS. 3 and 4, it is obvious that the degree of reduction of the ozone purification rate is greater as the gas contact probability is higher and the degree of reduction of the ozone purification rate is lesser as the gas contact probability is lower.

Figure 5:
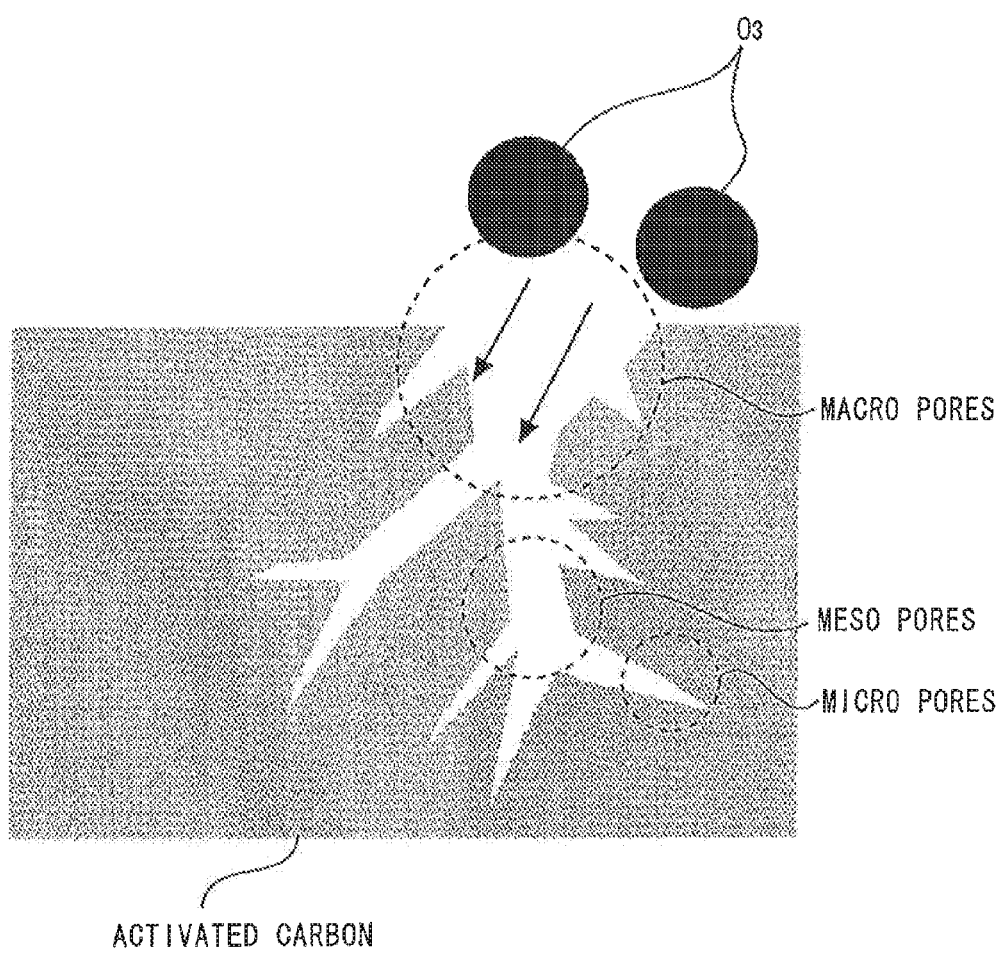
FIG. 5 shows the inner structure of the activated carbon.

The inventors assume that the ozone purification rate and the gas contact probability correlate with each other as described above because of the inner structure of the activated carbon and the ozonolysis mechanism of the activated carbon. The inner structure and the ozonolysis mechanism of the activated carbon will be explained with reference to FIG. 5. FIG. 5 shows the inner structure of the activated carbon. As shown in FIG. 5, the activated carbon has countless fine pores formed toward the inner side from the surface. The fine pores are divided into macro pores, meso pores, and micro pores depending on their sizes. When ozone molecules enter into such fine pores, electrons are provided from the activated carbon in the fine pores and the activation energy of an ozonolysis reaction is lowered. Consequently, ozone is converted into oxygen and active oxygen ($O_3 \rightarrow O_2 + O^*$).

In the air, various substances other than ozone exist and some substances eliminate the ozone purifying function of the activated carbon when entering into the fine pores. For example, oxygen, NOx, and PM containing ammonium nitrate act on as an oxidant of the activated carbon. Accordingly, when they enter into the fine pores as shown in FIG. 5, the activated carbon itself may be oxidized and its ozone purifying function may disappear. Also, active oxygen produced by the ozonolysis reaction of the activated carbon serves as an oxidant of the activated carbon. This active oxygen has stronger oxidizing power than the ozone, oxygen, NOx, and PM. Thus, when the active oxygen enters into the fin, pores of the activated carbon as shown in FIG. 5, it is extremely highly possible that the ozone purifying function of the activated carbon disappear.

Thus, the amount of the activated carbon coating the fin 20 is adjusted in the first embodiment. As described above with reference to FIG. 2, the air flowing in the radiator 14 becomes turbulent while reducing its flow rate. Accordingly, the probability that the above-described oxidant contacts with the fin 20 (hereinafter referred to as "oxidant contact probability") on the rear surface side is higher than that on the front surface side of the radiator 14.

Figure 6:
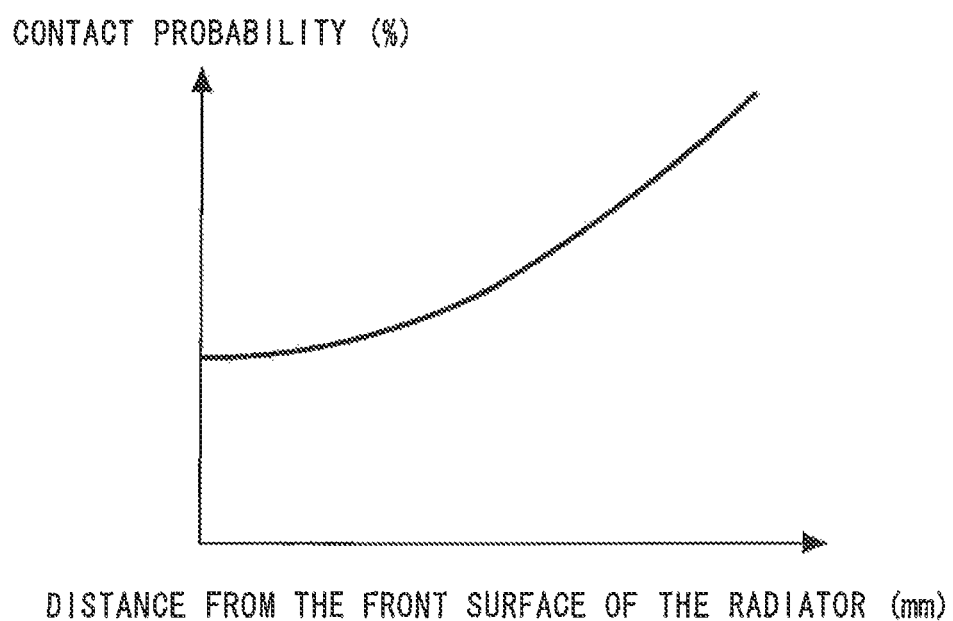
FIG. 6 shows a relationship between the distance (mm) from the front surface of the radiator 14 and the oxidant contact probability (%).

FIG. 6 shows a relationship between the distance (mm) from the front surface of the radiator 14 and the oxidant contact probability (%). As shown in FIG. 6, the oxidant contact probability is increased quadratically as the distance from the front surface of the radiator 14 becomes longer. Therefore, when the coating amount of the activated carbon on the front surface side of the radiator 14 is adjusted to be larger than the coating amount of the activated carbon on the rear surface side, oxidation of the activated carbon on the side where the oxidant contact probability is high can be favorably suppressed. By adjusting the coating amount of the activated carbon as described above, a certain surface area of the fin 20 contacting with the air directly on the rear surface side of the radiator 14 can be ensured. Thus, the cooling performance of the radiator 14 can be ensured. Further, the weight increase of the radiator 14 due to the coating of the activated carbon can be minimized.

Figure 7:
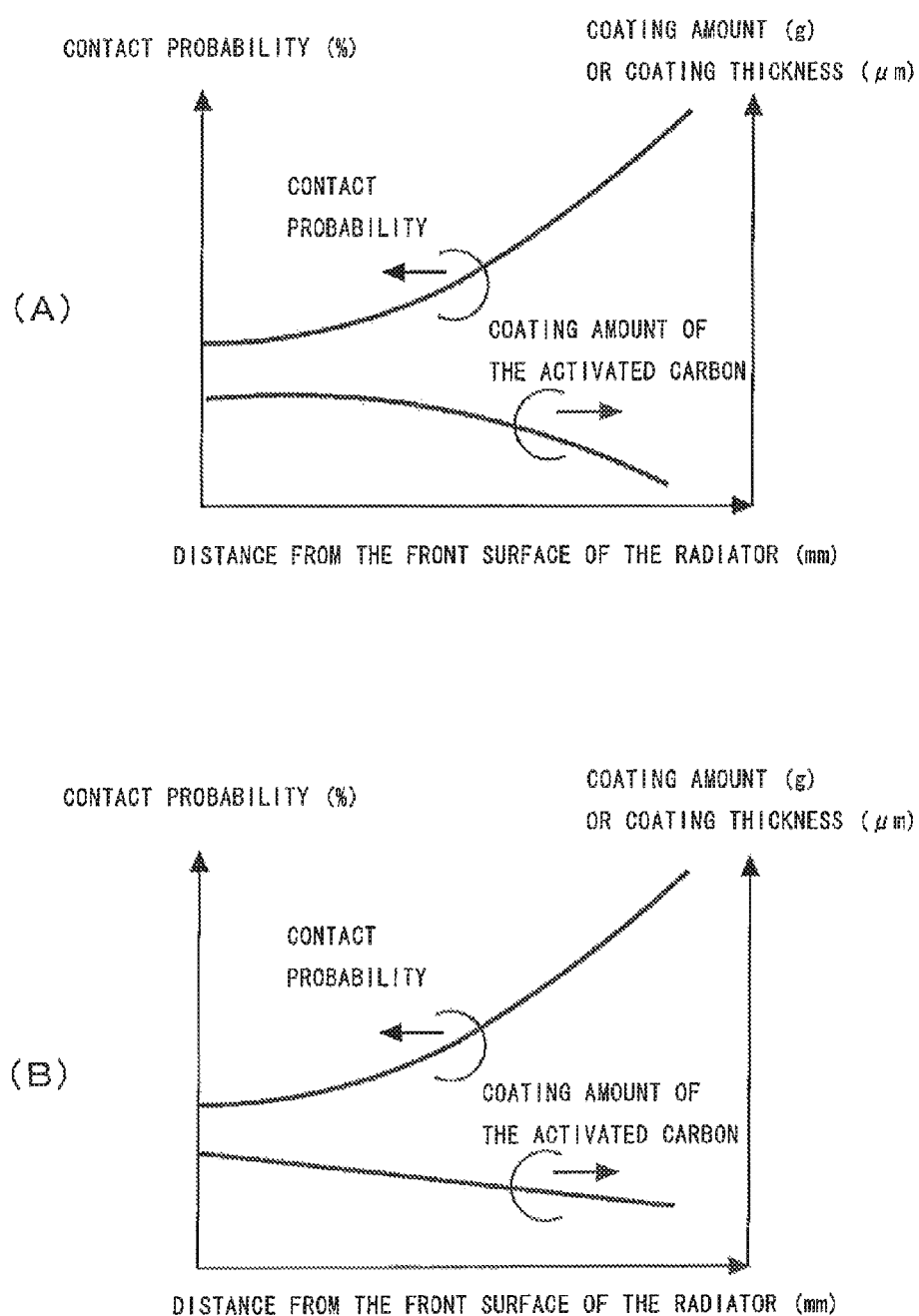
FIG. 7 shows specific examples of the coating amount (g) of the activated carbon coating the fin 20.

FIG. 7 shows specific examples of the coating amount (g) of the activated carbon coating the fin 20. As described above with reference to FIG. 6, the oxidant contact probability is increased quadratically as the distance from the front surface of the radiator 14 becomes longer. Thus, the coating amount of the activated carbon is reduced logarithmically or proportionally depending on the distance (mm) from the front surface side of the radiator 14 as shown in FIGS. 7(A) and 7(B). Incidentally, the coating thickness (μm) of the activated carbon may be adjusted instead of the coating amount of the activated carbon.

Figure 8:
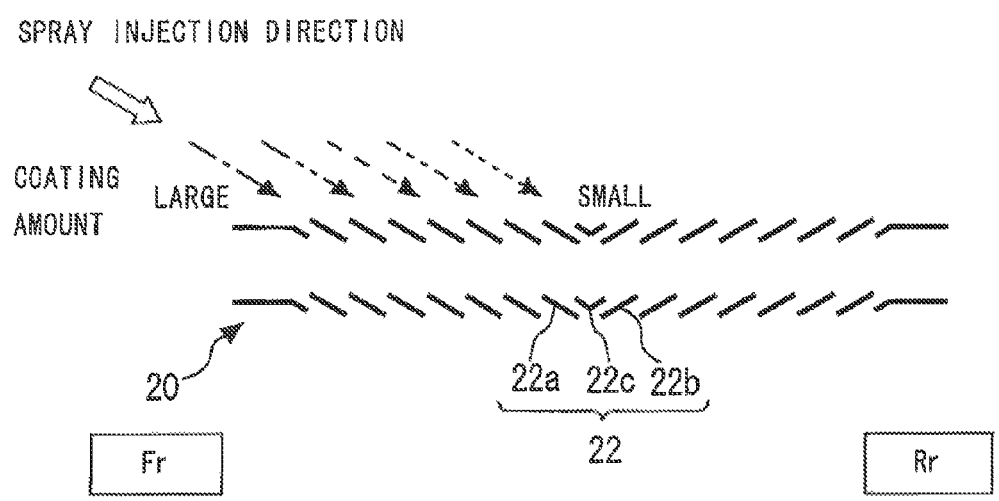
FIG. 8 is an illustration for explaining a method for manufacturing the air cleaner of the first embodiment.

Next, a method for manufacturing the air cleaner according to the first embodiment will be explained below with reference to FIG. 8. The air cleaner according to the first embodiment can be manufactured by a spraying method or a dip coating method. When the spraying method is used, activated carbon slurry is sprayed from the front surface side of the radiator 14 as shown in FIG. 8. Thus, the coating amount of the activated carbon on the front surface side of the radiator 14 can be larger than the coating amount of the activated carbon on the rear surface side. Incidentally, it is desirable that the spray injection pressure is determined to an optimal value by experiment or the like so that the coating amount of the activated carbon can be adjusted as described above. On the other hand, when the dip coating method is used, the radiator 14 is dipped in the activated carbon slurry and then pulled up from its rear surface side to adjust the coating time.

By using the air cleaner according to the first embodiment, the oxidation of the activated carbon on the side of the radiator 14 where the oxidant contact probability is higher can be favorably suppressed. Since the certain surface area of the radiator 14 on the rear surface side where the fin 20 contacts the air directly can be ensured, the cooling performance of the radiator 14 can be ensured. Further, the weight increase of the radiator 14 due to the coating of the activated carbon can be minimized.

Although the fin 20 is coated with the activated carbon in the first embodiment, it may be coated with elemental metal such as manganese, iron, cobalt, nickel, copper, ruthenium, and rhodium instead of the activated carbon. These elemental metals have an ozone purifying function as well as the activated carbon, but also have a property of being oxidized by the oxidant. Thus, when the fin 20 is coated with the elemental metal instead of the activated carbon, the above-described advantageous effects can be obtained. Incidentally, the fin 20 may be coated with two types or more of these elemental metals in combination, or may be coated with the elemental metals and the activated carbon simultaneously. This modification is similarly applicable to the later-described embodiments.

Although the radiator 14 includes the fin 20 in the first embodiment, the fin 20 is not always necessary. In other words, a honeycomb radiator in which cooling cores formed with fine flow paths are intensively arranged may be used instead of the radiator 14. In the case of using the honeycomb radiator, the wall surfaces of the flow paths are to be coated with the activated carbon. Therefore, the pressure loss of air flowing through the flow paths is increased toward the downstream, and its flow rate is reduced. Since the oxidant contact probability is increased toward the downstream, the above-described advantageous effects can be obtained by adjusting the coating amount of the activated carbon as described above in the first embodiment. This modification is similarly applicable to the later-described embodiments.

Second Embodiment

Next, the second embodiment of the present invention will be explained below with reference to FIG. 9. In the first embodiment, the coating amount of the activated carbon on the rear surface side of the radiator 14 is adjusted to be smaller than the coating amount of the activated carbon on the front surface side. Therefore, the ozone purifying capability on the rear surface side of the radiator 14 is reduced as compared to that on the front surface side. Thus, in the second embodiment, the surface of the activated carbon is coated with metal complex.

The metal complex coating the surface of the activated carbon is commonly known as a catalyst having an ozone purifying function and exhibiting resistance to the oxidant. The metal complex may be one type of metals selected from the group consisting of manganese, iron, cobalt, nickel, copper, ruthenium, rhodium, and palladium as a center metal. Two or more types of metals may be used in combination.

Figure 9:
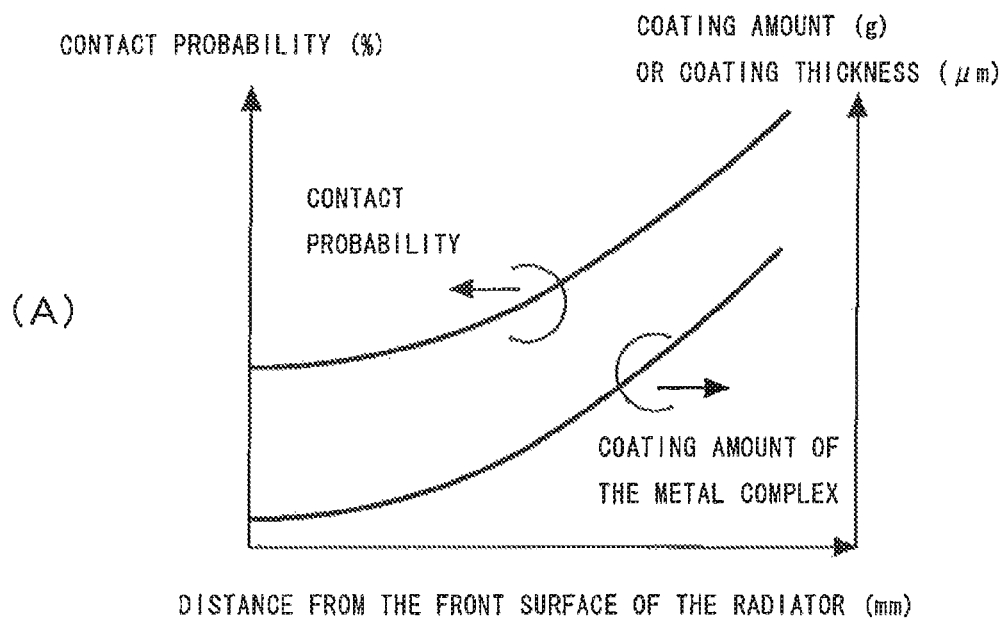
FIG. 9 shows specific examples of the coating amount (g) of the metal complex coating the fin 20 coated with the activated carbon.
Figure 9:
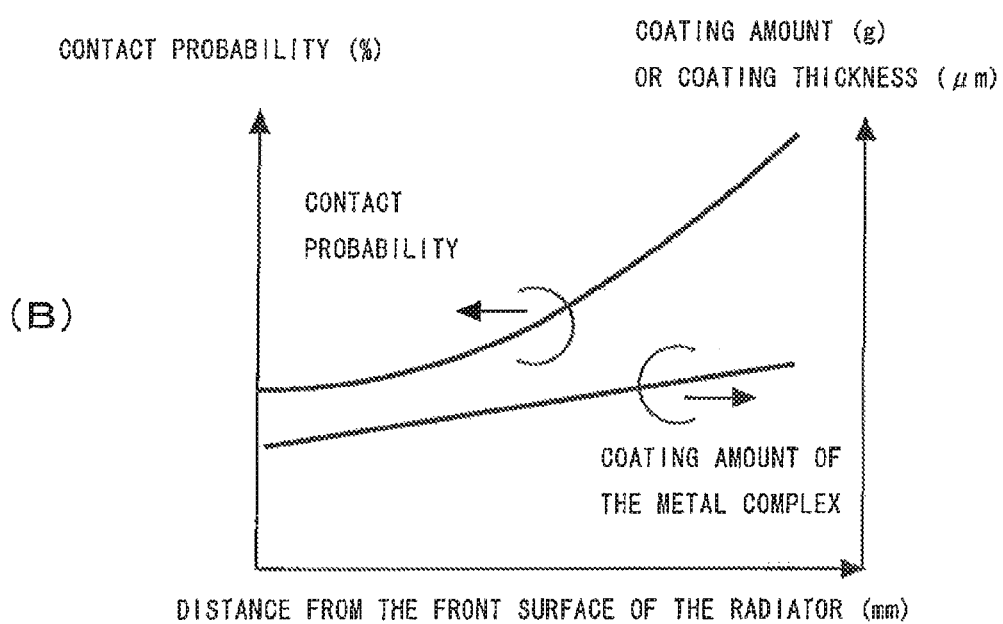

FIG. 9 shows specific examples of the coating amount (g) of the metal complex coating the fin 20 coated with the activated carbon. In the second embodiment, the coating amount of the metal complex is increased logarithmically or proportionally depending on the distance (mm) from the front surface side of the radiator 14 as shown in FIGS. 9(A) and 9(B). In other words, the coating amount of the metal complex is adjusted inversely with the coating amount of the activated carbon. Thus, the reduction of the ozone purifying capability on the rear surface side of the radiator 14 can be sufficiently suppressed.

An air cleaner according to the second embodiment can be manufactured by the spraying method or the dip coating method as in the first embodiment. When either method is used, the radiator 14 in which the coating amount of the activated carbon is adjusted according to the first embodiment is used. When the spraying method is used, the metal complex is sprayed from the rear surface side of the radiator 14. Accordingly, the coating amount of the metal complex on the rear surface side of the radiator 14 can be larger than the coating amount of the metal complex on the front surface side. On the other hand, when the dip coating method is used, the radiator 14 is dipped in the metal complex and then pulled up from the front surface side while adjusting the coating time.

Although the fin 20 is coated with the metal complex in the second embodiment, the fin 20 may be coated with metallo-organic complex instead of the metal complex. Alternatively, the fin 20 may be coated with palladium, silver, platinum, gold, or zeolite. These alternative materials have an ozone purifying function and exhibit resistance to the oxidant as well as the metal complex. The metallo-organic complex which can be used as the alternative material may be salen type, porphyrin type, phthalocyanine type, or phenanthroline type of one of the metals described as the center metal of the metal complex. Two types or more of them may be used in combination. Alternatively, they may be used with the metal complex. This modification is similarly applicable to the later-described embodiment.

In the second embodiment, the coating amount of the metal complex is adjusted inversely with the coating amount of the activated carbon. However, the coating amount of the metal complex is not necessarily adjusted in such a manner. In other words, the reduction of the ozone purifying capability can be suppressed as long as part of the surface of the activated carbon on the rear surface side of the radiator 14 is coated with the metal complex. Also, due to such coating, the weight increase of the radiator 14 caused by coating of the metal complex and the deterioration of the cooling performance of the radiator 14 can be minimized. This modification is similarly applicable to the later-described embodiment.

In the second embodiment, another activated carbon having a larger specific surface area than the activated carbon coating the fin 20 may be used instead of the metal complex. The ozone purifying capability is high when the specific surface area of the activated carbon is large. Accordingly, when activated carbon having a large specific surface area is used for coating, the reduction of the ozone purifying capability on the rear surface side of the radiator 14 can be suppressed. The activated carbon having the large specific surface area may be used with the metal complex or the metallo-organic complex. This modification is similarly applicable to the later-described embodiment.

Third Embodiment

Figure 10:
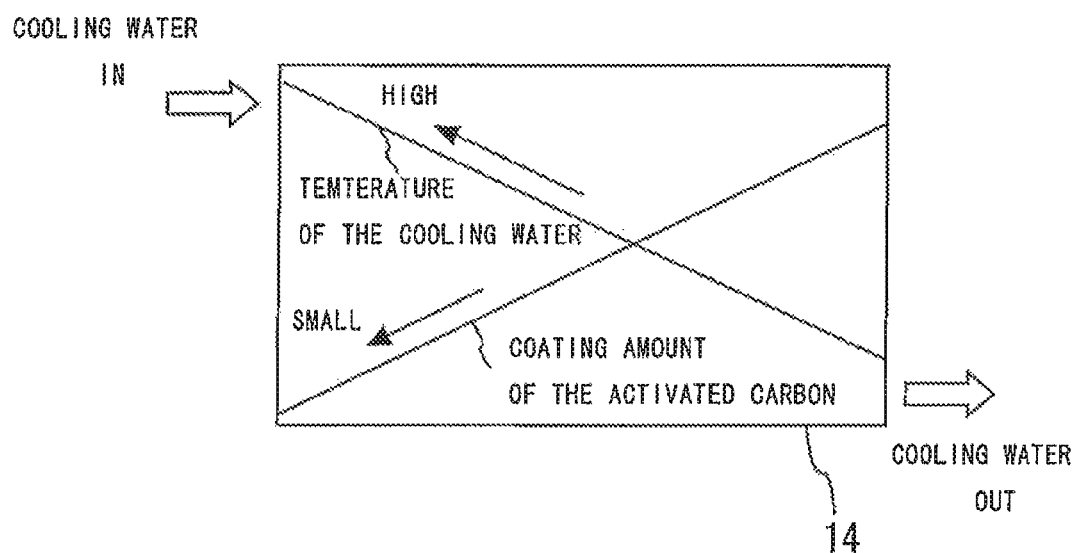
FIG. 10 shows a relationship between the temperature (° C.) of the cooling water in the radiator 14 and the coating amount (g) of the activated carbon.

Next, the third embodiment of the present invention will be explained below with reference to FIG. 10. In the third embodiment, it is characterized in that the coating amounts of the activated carbon or the metal complex on the upstream side and the downstream side of a cooling water path are adjusted on the basis of the first and second embodiments.

The cooling water path (not shown) for delivering cooling water in the internal combustion engine is formed within the radiator 14. The cooling water at high temperature is delivered from the internal combustion engine 12 into an inlet of the cooling water in the cooling water path. Accordingly, the reactivity of the ozonolysis reaction on the inlet of the cooling water is higher than that on an outlet. Thus, when comparing two fins 20 arranged at two different positions where the distances from the front surface of the radiator 14 are the same, the amount of produced active oxygen in the fin 20 close to the inlet of the cooling water is larger than that in the fin 20 close to the outlet. In other words, the oxidant contact probability on the downstream of the fin 20 close to the inlet of the cooling water is high.

Hence, in the third embodiment, the coating amount of the activated carbon on the inlet of the cooling water is adjusted to be smaller than the coating amount of the activated carbon on the outlet. FIG. 10 shows a relationship between the temperature (° C.) of the cooling water in the radiator 14 and the coating amount (g) of the activated carbon. As shown in FIG. 10, the temperature of the cooling water on the inlet is high, and becomes lower as the cooling water toward the outlet. By adjusting the coating amount of the activated carbon in such a manner shown in FIG. 10, the amount of produced active oxygen at the positions where the distances from the front surface of the radiator 14 are the same can be equalized. Thus, the oxidation of the activated carbon on the downstream of the fin 20 close to the inlet of the cooling water can be favorably suppressed.

In the third embodiment, the coating amount of the metal complex on the inlet of the cooling water is adjusted to be larger than the coating amount of the activated carbon on the outlet. By adjusting the coating amount of the metal complex in such a manner, the reduction of the ozone purifying capability on the inlet of the cooling water can be suppressed.

An air cleaner according to the third embodiment can be manufactured by the spraying method or the dip coating method as in the first or the second embodiment.

DESCRIPTION OF REFERENCE NUMERALS 10 vehicle
12 engine
14 radiator
16 capacitor
18 bumper grill
20 fin
22 louver
22a, b slant piece
22c bent piece

The invention claimed is:

1. A vehicular air cleaner, comprising:
a radiator including an air inlet into which air is delivered during travel of a vehicle, an air outlet through which the air delivered from the air inlet is discharged, an inner flow path connecting the air inlet and the air outlet, and a cooling water path for delivering cooling water therein; and
an ozone purifying material carried on a wall surface of the inner flow path for purifying ozone by converting the ozone into other substances,
wherein an amount of the carried ozone purifying material is adjusted such that the amount of the carried ozone purifying material on the air inlet side is larger than that on the air outlet side, and
wherein the amount of the carried ozone purifying material is adjusted such that the amount of the carried ozone purifying material on an outlet side of the cooling water path is larger than that on an inlet side of the cooling water path.

2. The vehicular air cleaner according to claim 1, further comprising an ozone purifying catalyst which is carried on the wall surface of the inner flow path and produced by a purifying function of the ozone purifying material, the ozone purifying catalyst having resistance to an oxidant which oxidizes the ozone purifying material while purifying the ozone by converting the ozone into other substances.

3. The vehicular air cleaner according to claim 2, wherein an amount of the carried ozone purifying catalyst is adjusted such that the amount of the carried ozone purifying catalyst on the air outlet side is larger than that on the air inlet side.

4. The vehicular air cleaner according to claim 2, wherein the ozone purifying catalyst includes at least one of a metal complex and a metallo-organic complex composed of manganese, iron, cobalt, nickel, copper, ruthenium, rhodium, or palladium as a center metal, palladium, silver, platinum, gold, and zeolite.

5. The vehicular air cleaner according to claim 1, wherein a specific surface area of the ozone purifying material is adjusted such that the specific surface area on the air outlet side is larger than that on the air inlet side.

6. The vehicular air cleaner according to claim 1, wherein the radiator includes a fin formed with louvers imparting turbulence to the air delivered from the air inlet.

7. The vehicular air cleaner according to claim 1, wherein the ozone purifying material includes at least one of activated carbon, manganese, iron, cobalt, nickel, copper, ruthenium, and rhodium.

* * * * *